(12) United States Patent
Chang

(10) Patent No.: US 8,286,879 B2
(45) Date of Patent: Oct. 16, 2012

(54) CONNECTOR OF FOR INSERTING SUBSCRIBER IDENTITY MODULE CARD

(76) Inventor: Nai-Chien Chang, Sanchong (TW)

( * ) Notice: Subject to any disclaimer, the term of this patent is extended or adjusted under 35 U.S.C. 154(b) by 444 days.

(21) Appl. No.: 12/577,380

(22) Filed: Oct. 12, 2009

(65) Prior Publication Data

US 2010/0155489 A1 Jun. 24, 2010

(30) Foreign Application Priority Data

Dec. 22, 2008 (TW) .................................. 97223008 U

(51) Int. Cl.
*G06K 7/00* (2006.01)
(52) U.S. Cl. ......................................... 235/486; 235/441
(58) Field of Classification Search ........................ None
See application file for complete search history.

(56) References Cited

U.S. PATENT DOCUMENTS

| 6,964,585 B2 * | 11/2005 | Blichasz et al. ............... 439/638 |
| 2008/0318446 A1 * | 12/2008 | Clancy et al. ................. 439/76.1 |
| 2010/0123006 A1 * | 5/2010 | Chen ............................. 235/441 |

* cited by examiner

*Primary Examiner* — Thien M. Le
*Assistant Examiner* — Sonji Johnson
(74) *Attorney, Agent, or Firm* — Chun-Ming Shih; HDLS IPR Services

(57) ABSTRACT

A connector for inserting a subscriber identity module (SIM) card includes a main body, a card reader and an electric connector. The main body includes at least two interfaces. The card reader is installed in one of the interfaces, and the card reader includes a card insertion mechanism and a printed circuit board. The electric connector is installed in another interface. After the SIM card is inserted into the card reader, a computer can be connected to a network to achieve a high-speed networking function at any place where a mobile phone can receive signals.

6 Claims, 6 Drawing Sheets

CONNECTOR OF FOR INSERTING SUBSCRIBER IDENTITY MODULE CARD

BACKGROUND OF THE INVENTION

1. Field of the Invention

The present invention relates to a connector, and more particular to a connector having a built-in card reader.

2. Description of Prior Art

Most electronic devices including notebook computers and desktop computers can log on the Internet through a network cable for uploading or downloading data through the network cable. Once the notebook or desktop computers cannot be connected to the network by using a network cable, users can log on the Internet by a wireless networking tool such as a wireless router, a wireless network card, a wireless application protocol (WAP). Since the notebook or desktop computers used for connecting the network are usually affected by densely located buildings or thick walls of the buildings, users cannot log on the Internet, and such application causes tremendous troubles to users.

In addition, subscriber identity module (SIM) card has been used extensively in mobile phones, credit cards, and healthcare insurance cards. Each GSM system mobile phone user obtains a SIM card from a related telecommunication service company, and the SIM card saves information including telephone number, telephone directory, call limitation, personal identity number (PIN) and personal unlocking key (PUK) of the related user, and the information is identical to the data stored in a database of a network system. A user has to use an authorized SIM card for the connection to a GSM communication system before the user can exchange data through a respective GSM communication network, or else the user cannot enter into the GSM system. As the number of base stations of mobile phones has been increased drastically to enhance the signal receiving capability and quality of the mobile phones, it is an important subject for related manufacturers to integrate a SIM card into a notebook or desktop computer in order to log on the Internet at any place wherein the mobile phone can receive signals, such that the notebook or desktop computer can have a high speed networking function immediately.

SUMMARY OF THE INVENTION

Therefore, it is an objective of the present invention to provide a card reader coupled with a connector, wherein the connector is connected to a transmission line or a wireless card, and the card reader is provided for users to insert the SIM card, and a notebook or desktop computer is connected to the Internet at any place where a mobile phone can receive signals, so that the notebook or desktop computer can have a high speed networking function, and the present invention provides users another alternative of wireless networking function.

To achieve the foregoing objective, the present invention provides a connector for inserting a subscriber identity module (SIM) card, and the connector comprises:

a main body, having at two interfaces disposed thereon, two interfaces, a partition plate installed between the two interfaces, a plurality of embedding slots disposed at a distal side of the partition plate, a plurality of positioning slots formed on the bottom plate of one of the two interfaces, and a cover plate coupled and covered onto an opening at an end of the two interfaces, and an open slot formed at a front end of the other one of the two interfaces;

a card reader, installed in one of the two interfaces, and comprised of a card insertion mechanism and a printed circuit board, and installed in one of the interfaces, and the card insertion mechanism including a base, and the base including an insert slot, and the insert slot including two pressing plates extended from both lateral sides of the insert slot and corresponding to the insert slot, and the insert slot including a plurality of notches, each being embedded with a conductive spring plate, and the conductive spring plate including a first terminal and a second terminal, and the first terminal of the conductive spring plate being extended into the insert slot, and the second terminal being disposed at the bottom of the notch; the printed circuit board including a plurality of soldering points disposed thereon, and electrically coupled to the first terminal of the conductive spring plate, and a terminal of the printed circuit board being electrically coupled to an antenna, a wireless module and a plurality of conductive pins, and the card reader being embedded into the main body, and the conductive pin of the printed circuit board of the card reader including an embedding slot embedded into the partition plate; and an electric connector, installed at the other one of the two interfaces, and having a plurality of metal pins, and after the electric connector is embedded into the main body, the metal pin of the electric connector is positioned into the positioning slot of the bottom plate.

DETAILED DESCRIPTION OF THE INVENTION

The technical characteristics, features and advantages of the present invention will become apparent in the following detailed description of the preferred embodiments with reference to the accompanying drawings. The drawings are provided for reference and illustration only, but not intended for limiting the present invention.

Figure 1:
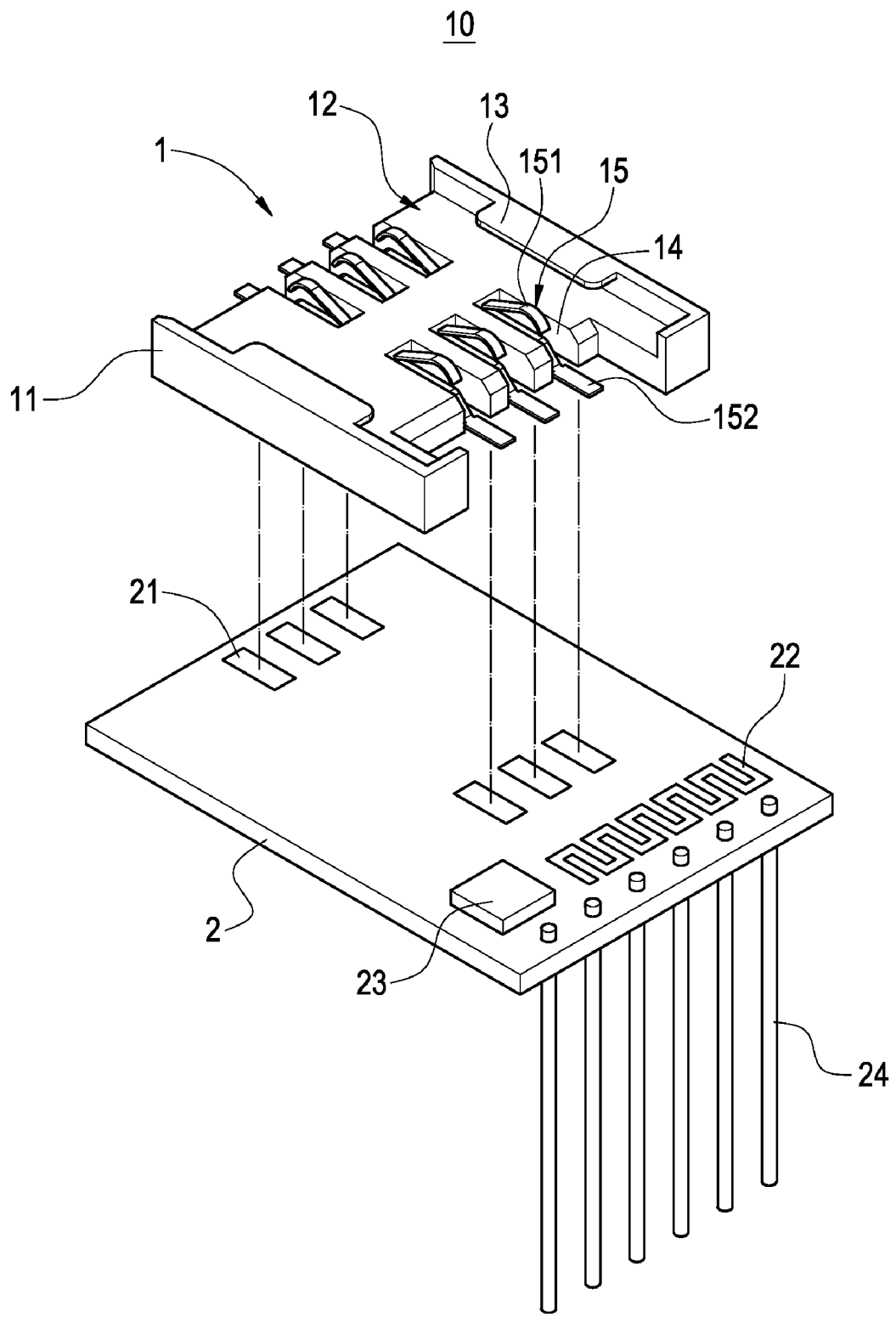
FIG. 1 is an exploded view of a card reader of the present invention.

With reference to FIG. 1 for an exploded view of a card reader of the present invention, the present invention is a connector for inserting a subscriber identity module card, wherein the card reader 10 in the connector comprises a card insertion mechanism 1 and a printed circuit board 2.

The card insertion mechanism 1 includes a base 11, and the base 11 includes an insert slot 12 thereon, and two pressing plates 13 extended from both sides of the insert slot 12 and corresponding to the insert slot 12, and the insert slot 12 includes a plurality of notches 14, each having a conductive spring plate 15 embedded therein, and the conductive spring plate 15 includes a first terminal 151 and a second terminal 152, and the first terminal 151 of the conductive spring plate 15 is extended into the insert slot 12, and the second terminal 152 is disposed at the bottom of the notch 14. After the SIM card is inserted into the insert slot 12, the pressing plate 13 can prevent the SIM card from being ejected by the first terminal 151 of the conductive spring plate 15.

The printed circuit board 2 includes a plurality of soldering points 21 electrically coupled to the first terminal 151 of the conductive spring plate 15. A terminal of the printed circuit board 2 is electrically coupled to an antenna 22, a wireless module 23 and a plurality of conductive pins 24. After the conductive pins 24 are electrically coupled to an electronic device (not shown in the figure), and the SIM card is inserted into the insert slot 12 of the card insertion mechanism 1, the communication system of the electronic device is turned on, and the wireless module 23 can emit and receive signals.

Figure 2:
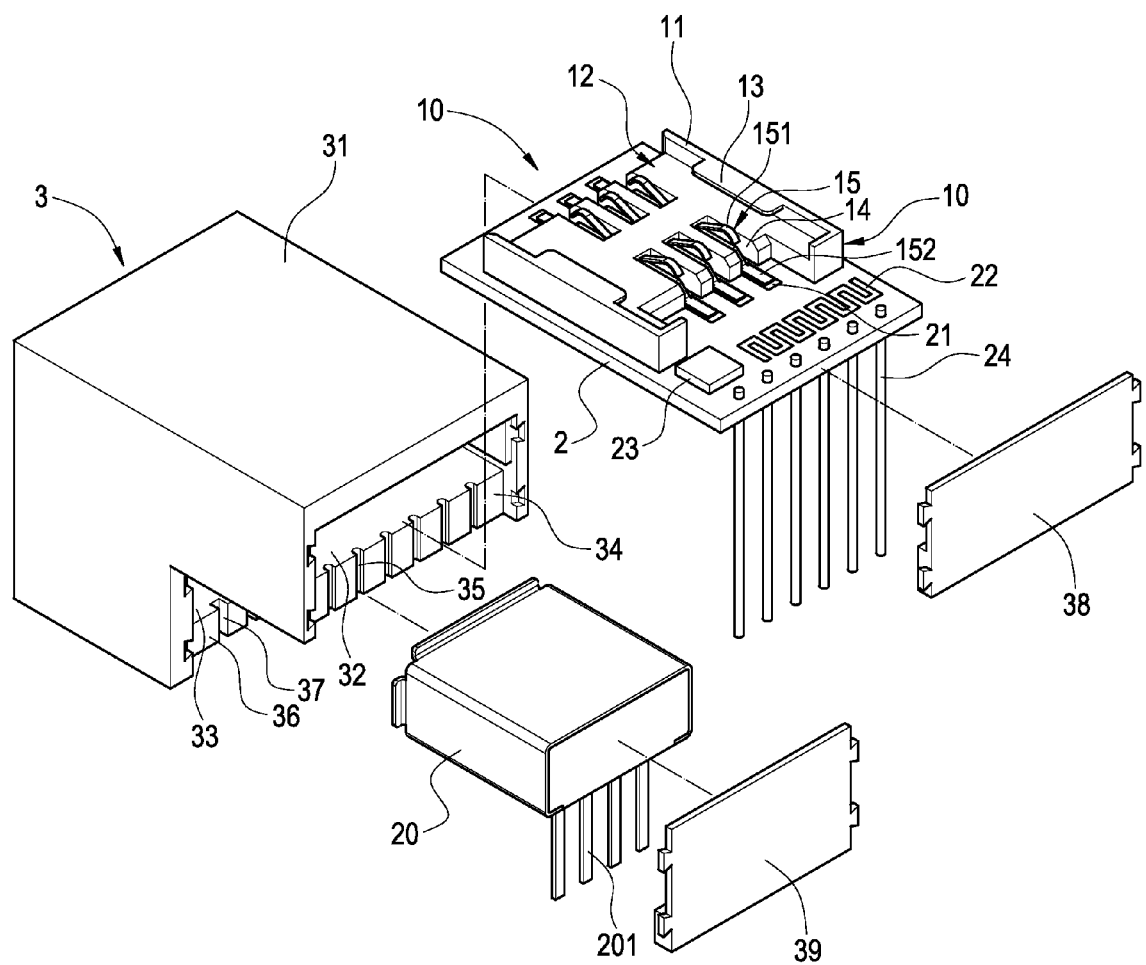
FIG. 2 is an exploded view of connecting a card reader, an electric connector and a connector in accordance with the present invention.
Figure 3:
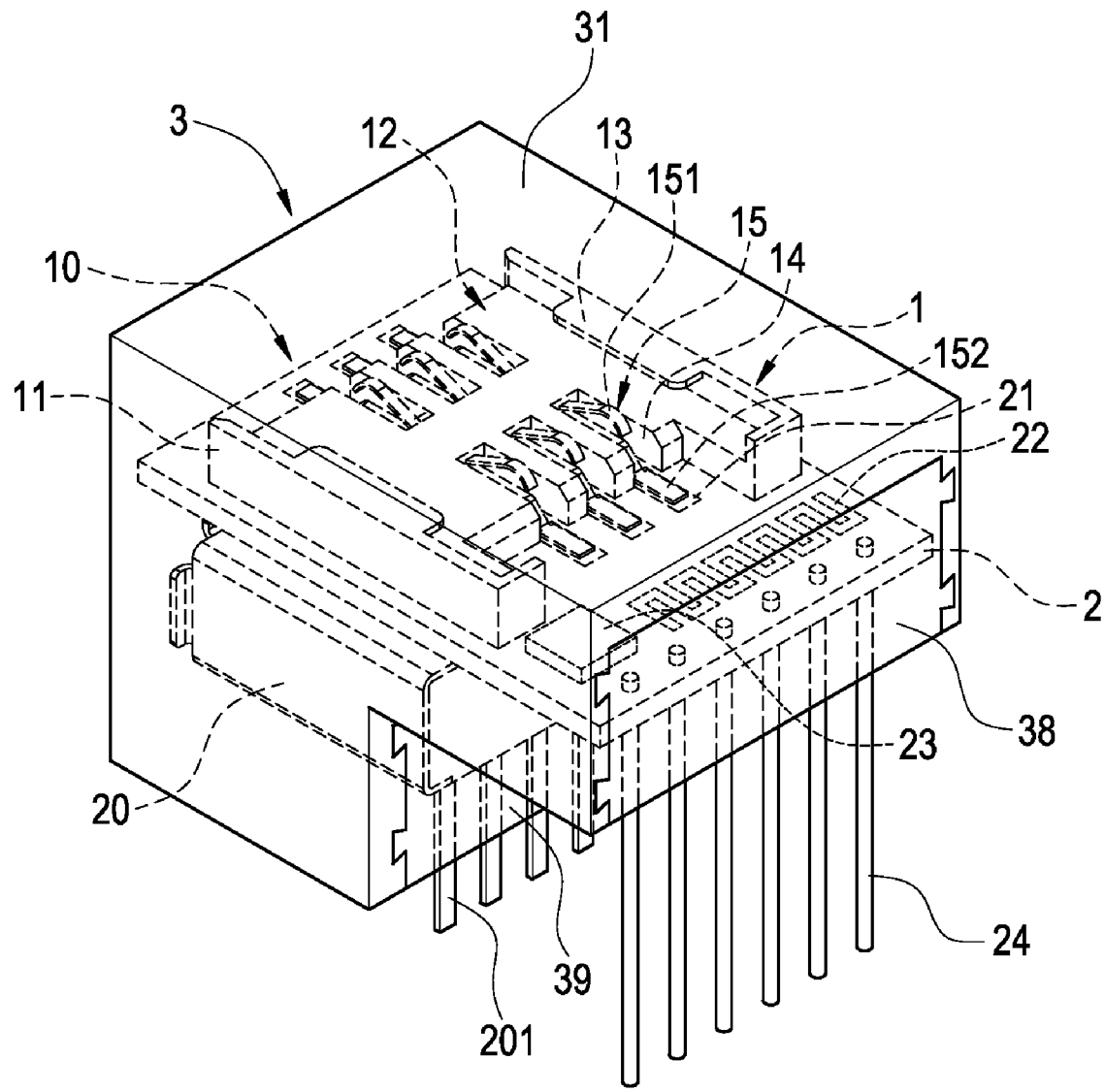
FIG. 3 is a rear view of a card reader, an electric connector and a connector after being installed in accordance with the present invention.

With reference to FIGS. 2 and 3 for an exploded view and a rear view of connecting a card reader, an electric connector and a connector in accordance with the present invention respectively, the connector 3 includes a main body 31 of an inverted L-shaped body, and the main body 31 includes a first interface 32 and a second interface 33, and a partition plate 34 installed between the first and second interfaces 32, 33, and a distal side of the partition plate 34 includes a plurality of embedding slots 35, and the bottom of the second interface 33 includes a plurality of positioning slots 37. The first interface 32 is provided for embedding the card reader 10 into the main body 31, and the conductive pin 24 on the printed circuit board 2 of the card reader 10 includes an embedding slot 35 embedded into the partition plate 34. The second interface 33 is provided for embedding the electric connector 20 into the main body 31, such that metal pins 201 of the electric connector 20 can be positioned in the positioning slot 37 of the bottom plate 36. After the card reader 10 and the electric connector 20 are installed at the first and second interfaces 32, 33, each opening of the first and second interfaces 32, 33 is covered by a cover plate 38, 39 for preventing the card reader 10 from being separated from the electric connector 20. In the figures, the electric connector 20 is a USB, HDMI, Displayport, PS/2, eSATA, micro-USB, MINI USB, or IEEE1394 connector.

Figure 4:
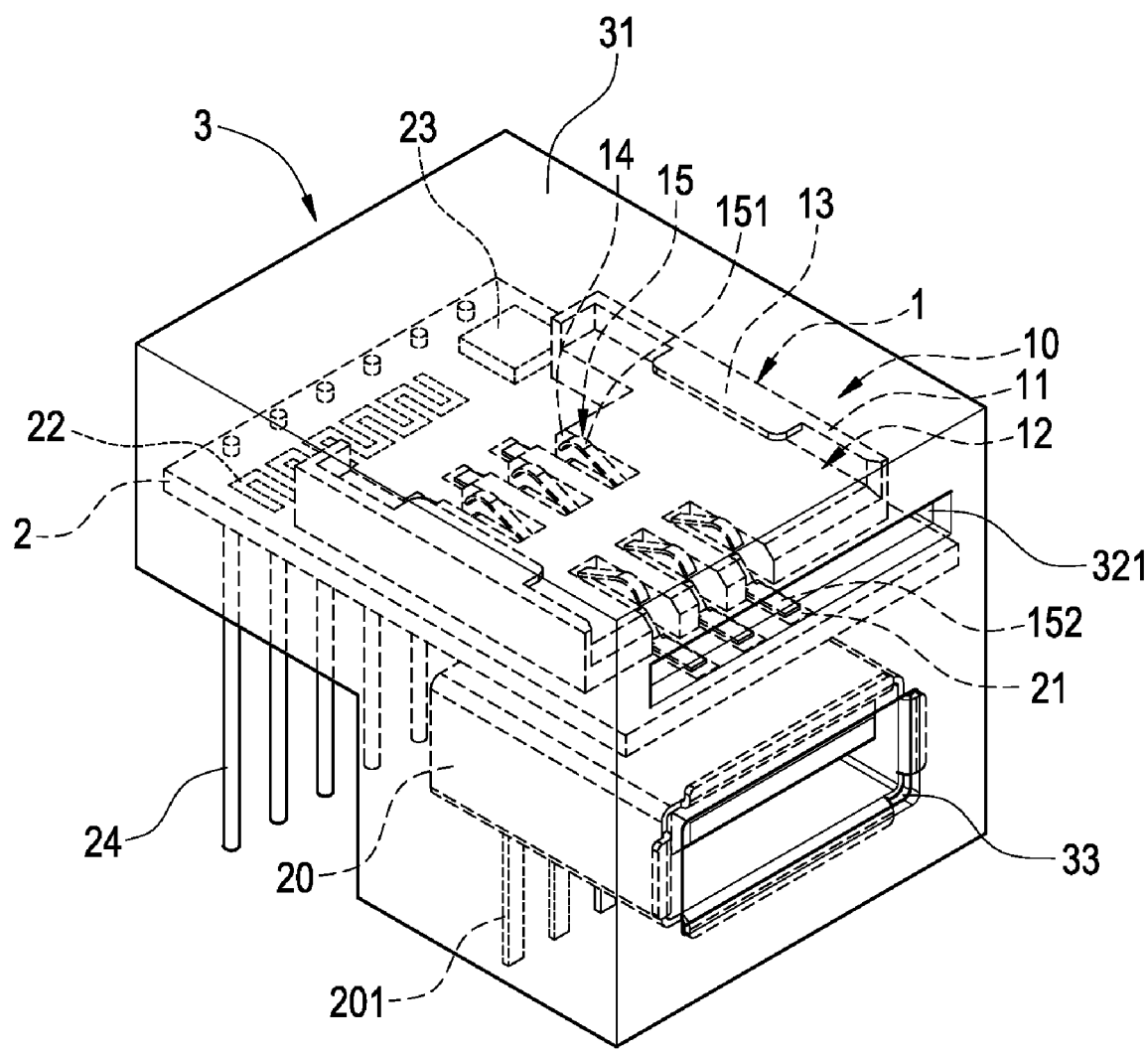
FIG. 4 is a perspective view of a connector of the present invention.
Figure 5:
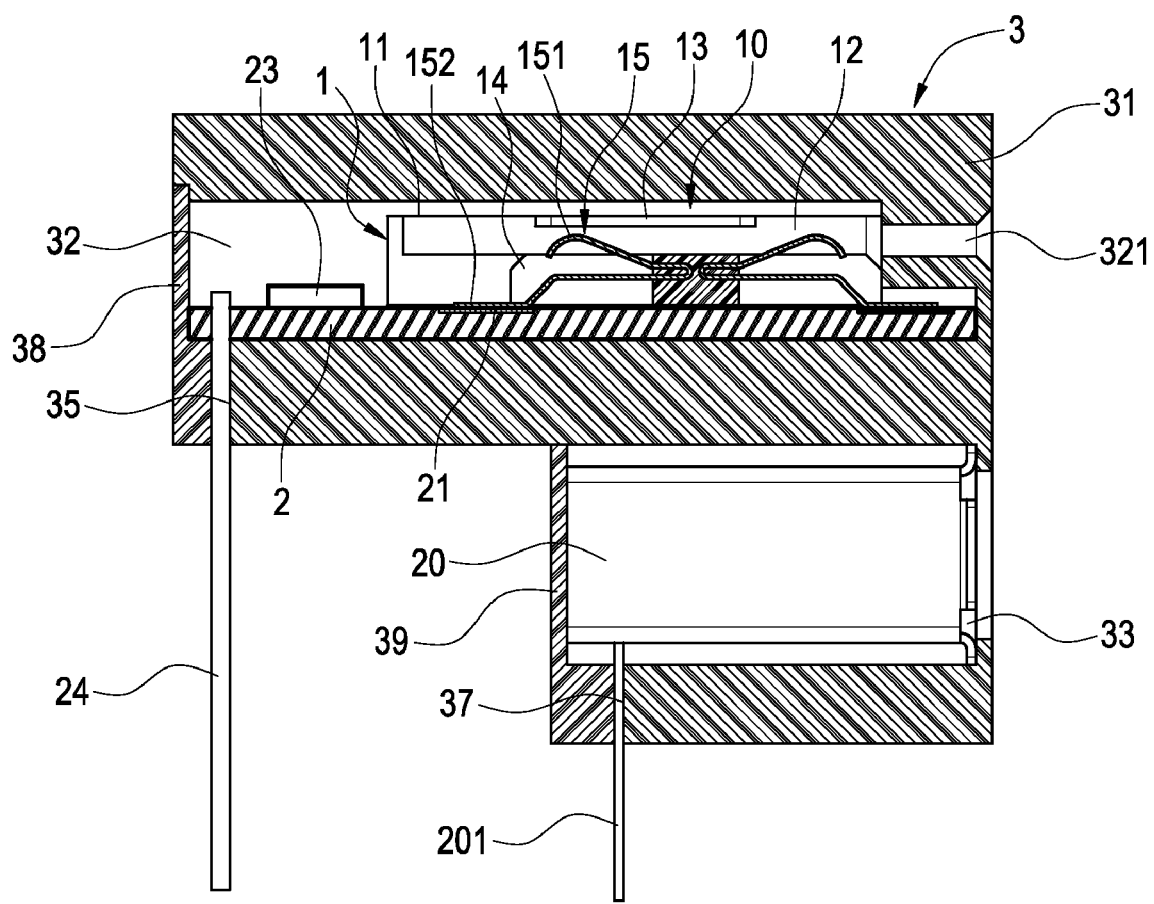
FIG. 5 is a cross-sectional side view of a connector of the present invention.

With reference to FIGS. 4 and 5 for a perspective view and a side view of a connector in accordance with the present invention, after the connector 3, the card reader 10 and the electric connector 20 are installed, a SIM card open slot 321 is formed at a front side of the first interface 32 of the connector 3, and the second interface 33 is provided for inserting a plug of a transmission line (not shown in the figure) and electrically coupling the electric connector 20. In the figures, the transmission line is a USB, HDMI, Displayport, PS/2, eSATA, micro-USB, MINI USB or IEEE1394 transmission line.

Figure 6:
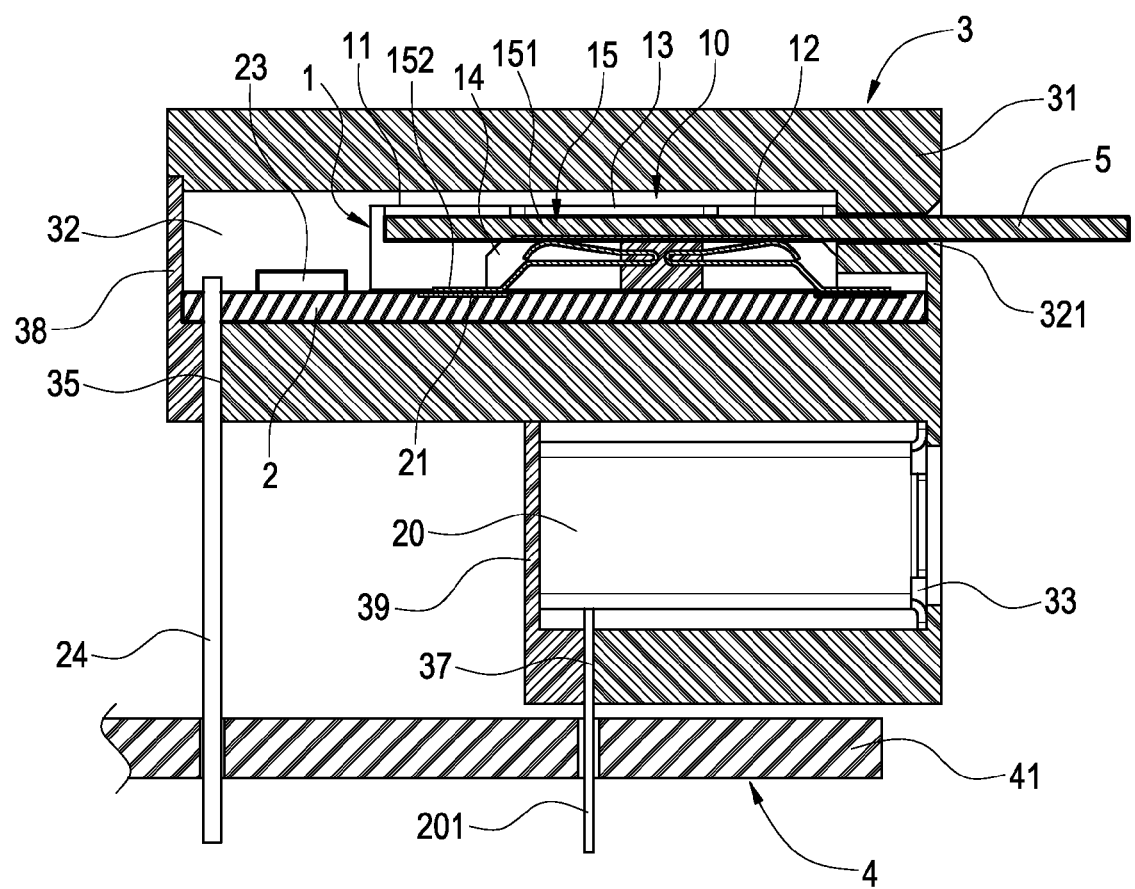
FIG. 6 is a schematic view of using a connector of the present invention.

With reference to FIG. 6 for an application of a connector in accordance with the present invention, if the connector 3 is electrically coupled to the main board 41 of the electronic device 4 (which is a notebook computer in this embodiment), such that after the SIM card 5 is inserted from the open slot 321, and the SIM card is electrically connected to the plurality of conductive spring plates 15 of the card reader 10, users can log on the Internet through the notebook computer at any place where the mobile phone can receive signals, and the users can have the access to a 3.5G high speed networking function.

The present invention is illustrated with reference to the preferred embodiment and not intended to limit the patent scope of the present invention. Various substitutions and modifications have suggested in the foregoing description, and other will occur to those of ordinary skill in the art. Therefore, all such substitutions and modifications are intended to be embraced within the scope of the invention as defined in the appended claims.

What is claimed is:

1. A connector device fixedly installed on an electronic device, comprising:
    a main body, having two accommodating rooms formed therein;
    a subscriber identity module (SIM) card reader, including a card insertion mechanism and a printed circuit board, and installed in one of the accommodating rooms, and the card insertion mechanism including a base, and the base including an insert slot, and two pressing plates extended from both lateral sides of the insert slot and corresponding to the insert slot, and the insert slot including a plurality of notches, each being embedded with a conductive spring plate, and the conductive spring plate including a first terminal and a second terminal, and the first terminal of the conductive spring plate being extended into the insert slot, and the second terminal being disposed at the bottom of the notch; the printed circuit board including a plurality of soldering points disposed thereon, and each electrically coupled to the second terminal of the conductive spring plate, and a side of the printed circuit board being electrically coupled to an antenna, a wireless module and a plurality of conductive pins; and
    an electric connector, installed in the other one of the accommodating rooms.

2. The connector of claim 1, wherein the main body is an inverted L-shaped body, a partition plate is installed between the two accommodating rooms, a plurality of embedding slots are disposed at a distal side of the partition plate, a plurality of positioning slots are formed on a bottom plate of the main body, and a cover plate is coupled and covered onto an opening at an end of each accommodating room.

3. The connector of claim 2, further comprising an open slot disposed at a front side of each accommodating room.

4. The connector of claim 2, wherein the SIM card reader is embedded into the main body, and the conductive pins on the printed circuit board pass through the embedding slots of the partition plate, respectively.

5. The connector of claim 2, wherein after the electric connector is embedded into the main body, a plurality of metal pins of the electric connector pass through the positioning slots of the bottom plate, respectively.

6. The connector of claim 1, wherein the electric connector is selected from the group consisting of USB, HDMI, Displayport, PS/2, eSATA, micro-USB, MINI USB and IEEE1394 connector.

* * * * *